United States Patent
Pregenzer et al.

(10) Patent No.: US 9,681,935 B2
(45) Date of Patent: Jun. 20, 2017

(54) INCONTINENCE IMPLANT

(71) Applicant: Lukas Pregenzer, Mieming (AT)

(72) Inventors: Lukas Pregenzer, Mieming (AT);
Bruno Pregenzer, Mieming (AT);
Arnulf Stenzel, Tübingen (DE)

(73) Assignee: Lukas Pregenzer (AT)

( * ) Notice: Subject to any disclaimer, the term of this patent is extended or adjusted under 35 U.S.C. 154(b) by 192 days.

(21) Appl. No.: 14/411,661

(22) PCT Filed: Apr. 26, 2013

(86) PCT No.: PCT/EP2013/001264
§ 371 (c)(1),
(2) Date: Dec. 29, 2014

(87) PCT Pub. No.: WO2014/000838
PCT Pub. Date: Jan. 3, 2014

(65) Prior Publication Data
US 2015/0173881 A1   Jun. 25, 2015

(30) Foreign Application Priority Data
Jun. 29, 2012   (DE) .................... 20 2012 006 290 U

(51) Int. Cl.
*A61F 2/00* (2006.01)
(52) U.S. Cl.
CPC .......... *A61F 2/0036* (2013.01); *A61F 2/0022* (2013.01)
(58) Field of Classification Search
CPC ........ A61F 2/0036; A61F 2/02; A61F 2/0022; A61F 2/004
See application file for complete search history.

(56) References Cited

U.S. PATENT DOCUMENTS

| 2002/0049364 A1* | 4/2002 | Pregenzer ............. A61F 2/0036 600/30 |
| 2008/0073903 A1 | 3/2008 | Bogh-Soerensen |
| 2010/0324572 A1* | 12/2010 | Needleman ............ A61B 17/10 606/142 |

FOREIGN PATENT DOCUMENTS

| EP | 0 639 355 A1 | 7/1994 |
| EP | 1 154 732 B1 | 1/2000 |

OTHER PUBLICATIONS

International Search Report corresponding to International Application No. PCT/EP2013/001264, dated Jul. 15, 2013; (4 total pages).

* cited by examiner

*Primary Examiner* — Christine H Matthews
(74) *Attorney, Agent, or Firm* — Carter, DeLuca, Farrell & Schmidt, LLP

(57) ABSTRACT

The invention relates to an implantable actuation mechanism, which can be switched between two stable positions, for an implant which can be switched between states or positions, having a support element which has an assembly plate for support at a bone and having a spring-loaded actuation element which is movable relative to the support element, which extends through the support element and which is connected by means of a cable to an activation part initiating a change between the two positions of the implant and provided at the other side of the support element. In accordance with the invention, the spring-loaded actuation element has a guide ring having more than one prolongation, wherein the prolongations are guided in a guide link such that they can latch into two latch positions defining the aforesaid positions under a spring load.

9 Claims, 7 Drawing Sheets

Figure 1:
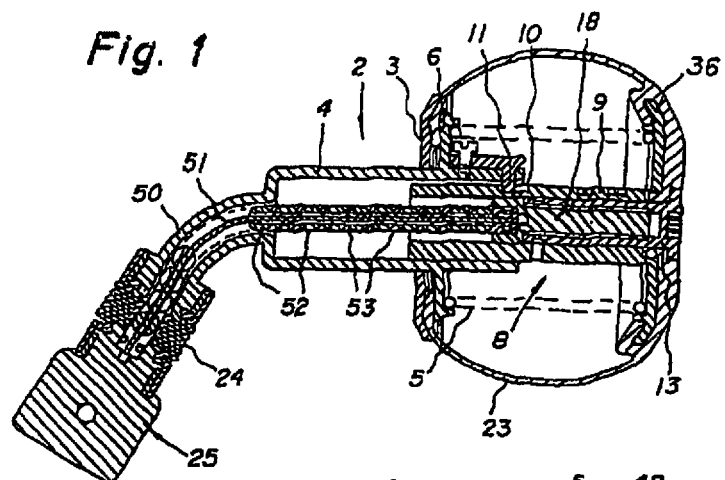

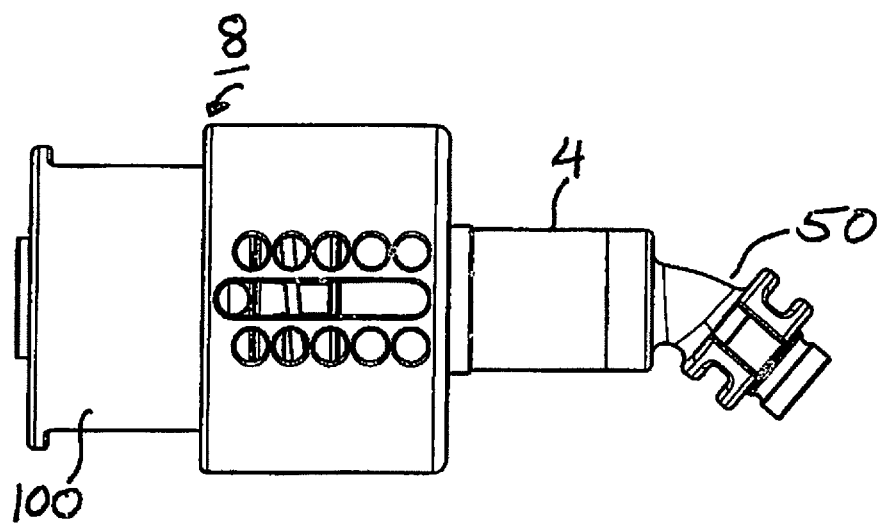
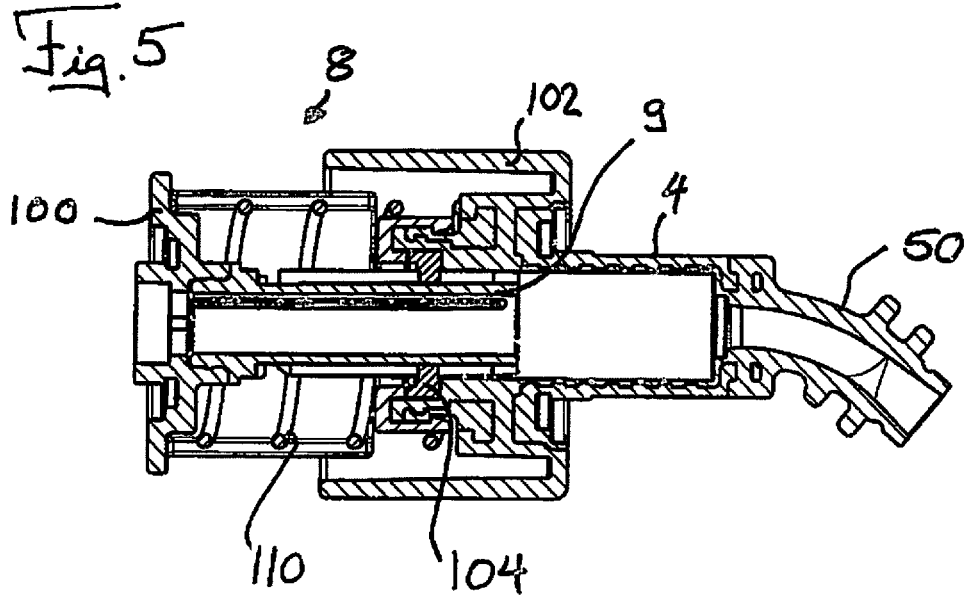

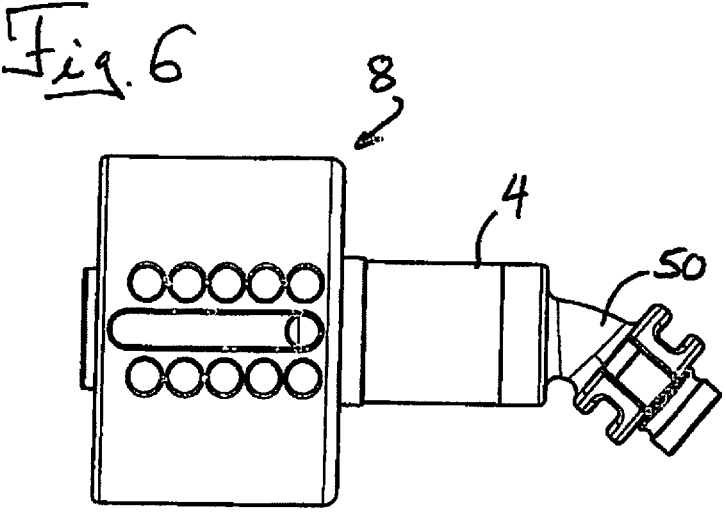
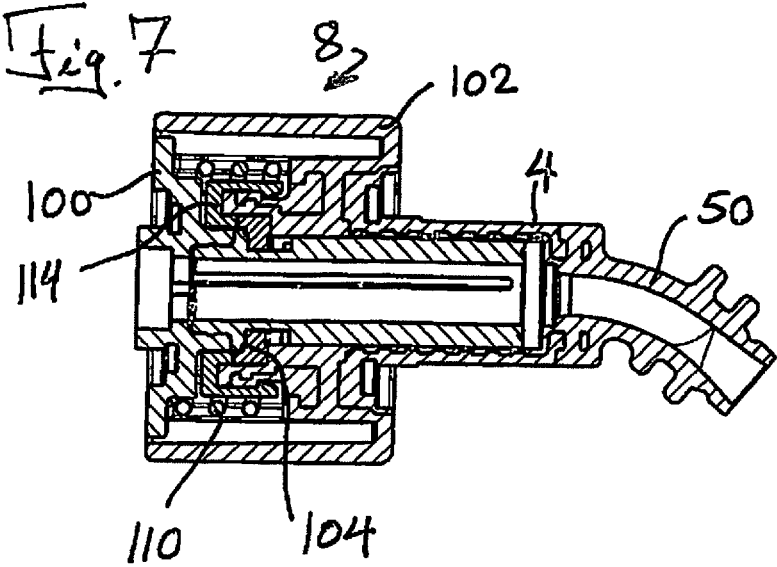

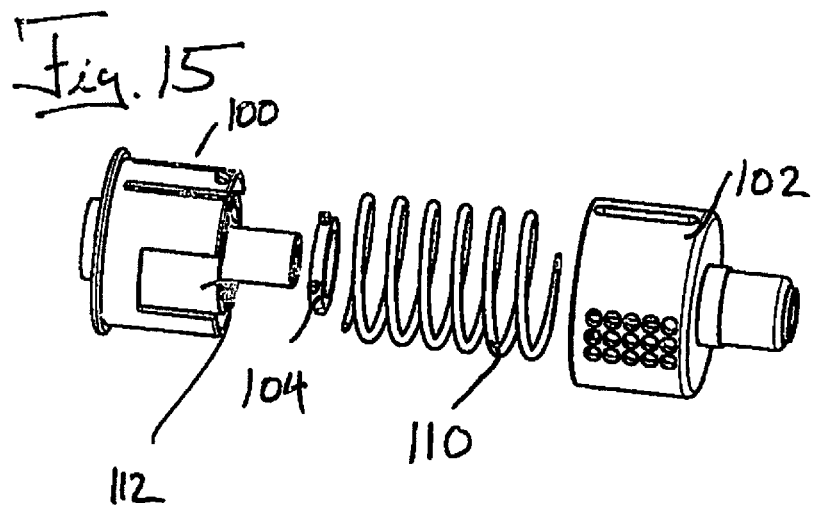
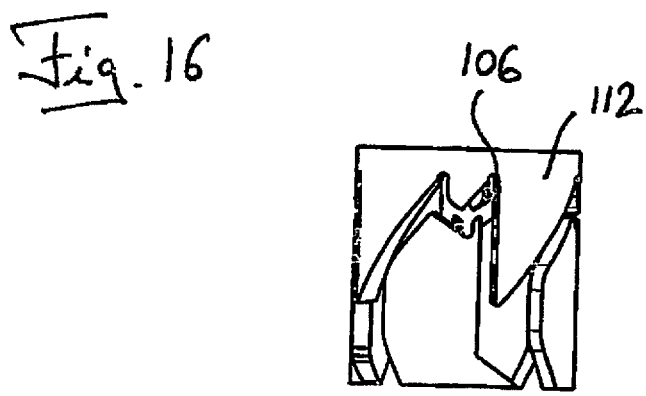
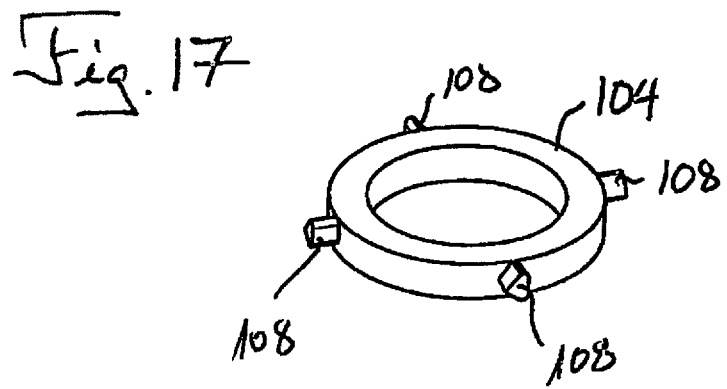

INCONTINENCE IMPLANT

The invention relates to an implantable actuation mechanism, which can be switched between two stable positions, for an implant which can be switched between two states or positions, having a support element which has an assembly plate for support at a bone and having a spring-loaded actuation element which is movable relative to the support element, which extends through the support element and which is connected by means of a cable to an activation part initiating a change between the two positions of the implant and provided at the other side of the support element.

A sling comprising a biocompatible foreign material and engaging beneath the urethra for preventing urinary incontinence is provided in EP-A-639 355, wherein the band ends are fixed at a higher position in the body and the center region of the sling represents a chamber which can be filled with a fluid, wherein the quantity of the filled-in fluid determines the support level of the urethra and can therefore likewise be adjusted. It is also stated in EP-A 639 355 that fasciae which are fixed in the body have already been used for the forming of a band loop. A later correction due to changes is, however, practically impossible.

U.S. Pat. No. 5,518,504 A shows a further implantable actuation mechanism. Here, a sling engaging beneath the urethra is likewise lowered from an elevated position of rest by means of a hydraulic system comprising a reciprocating pump pair.

The disadvantages of this device can be found in the use of a pressure fluid and the hoses to be laid and the risk of leakage with the necessity of a reservoir to be implanted. An actuation mechanism of the initially named kind for a closure device for natural, tube-like body organs can be seen, for example, from EP 1 154 732 B1. An implantable actuation mechanism has already been created here which actuates an implant which can be switched between two states or positions without a hydraulic system and in particular prevents urinary incontinence. However, in this already known actuating mechanism, an actuation element has been inserted in which a guide sleeve having a heart-shaped guide track is provided along which an individual guide pin slides and hereby results in the respective latching in a defined latch position of the actuation element under a spring load. It has been found that this latch mechanism cannot withstand a long-term load.

It is therefore the object of the invention to further develop an implantable actuation mechanism of this category such that it also works precisely in long-term operation despite long operating times.

This object is achieved in accordance with the invention by the combination of the features of claim 1.

Accordingly, an implantable actuation mechanism which can be switched between two stable positions is provided for an implant which can be switched between states or positions, wherein the spring-loaded actuation element has a guide ring having more than one prolongation, wherein the prolongations are guided in a guide link such that they can latch into two latch positions defining the aforesaid positions under spring load.

In accordance with the invention, the aforesaid one-dimensional guide part is therefore replaced with a multi-dimensional guide part. The wear due to the long-term load can hereby be substantially reduced so that the implantable actuation mechanism ensures a substantially longer period of use without another intervention in the patient having to be provided.

Preferred embodiments of the actuation mechanism result from the dependent claims following on from the main claim.

The guide ring is accordingly advantageously connected to a guide sleeve of the actuation element. The guide link, in contrast, can be provided in an inner sleeve of the actuation element or in a separate intermediate sleeve connected thereto.

The prolongations can either be arranged on the inner side of the guide ring or, however, in a constructional reversal, on the outer side of the respective guide ring. The prolongations have a substantially triangular cross-section. The prolongations are each arranged at the guide ring such that they are in areal contact with the guide link in which they engage. The wear of individual elements is hereby avoided.

The guide ring can particularly advantageously be installed longitudinally displaceably on the guide sleeve via a snap-in element which can snap onto the guide sleeve. A particularly simple and cost-efficient installation is hereby possible.

A particularly wear-minimized embodiment of the guide ring has four prolongations which are advantageously evenly distributed over the periphery of the guide ring.

Figure 2:
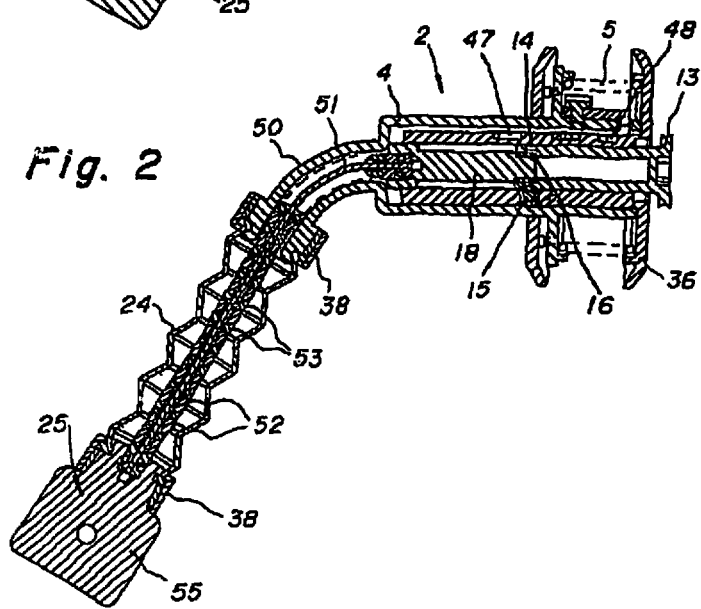
Figure 3:
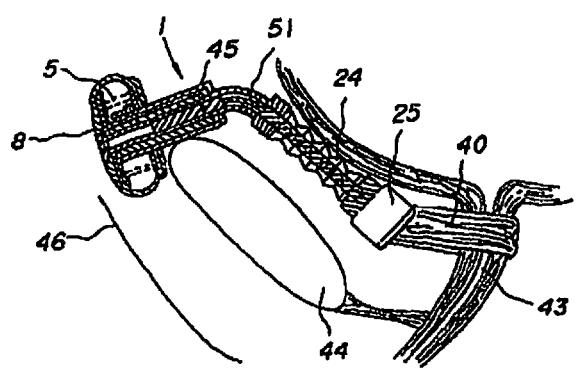
Figure 8:
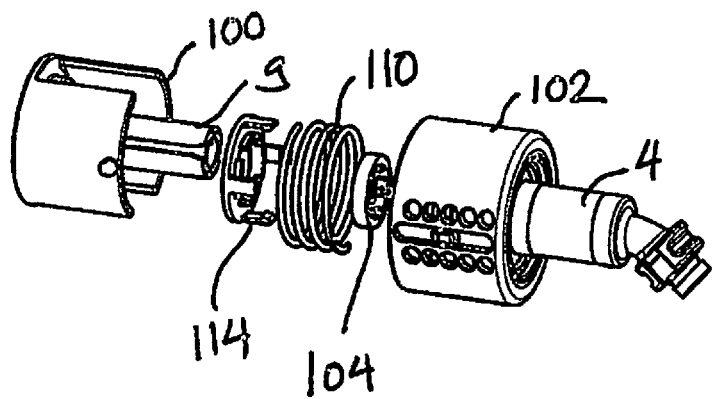
Figure 9:
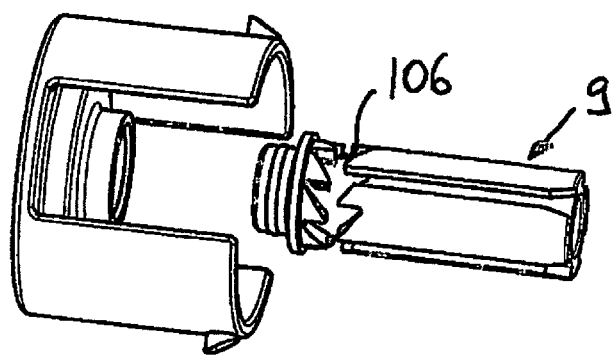
Figure 10:
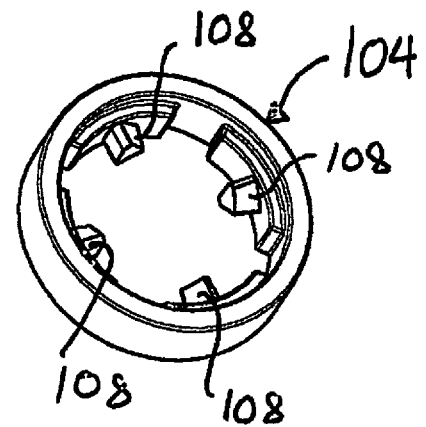
Figure 11:
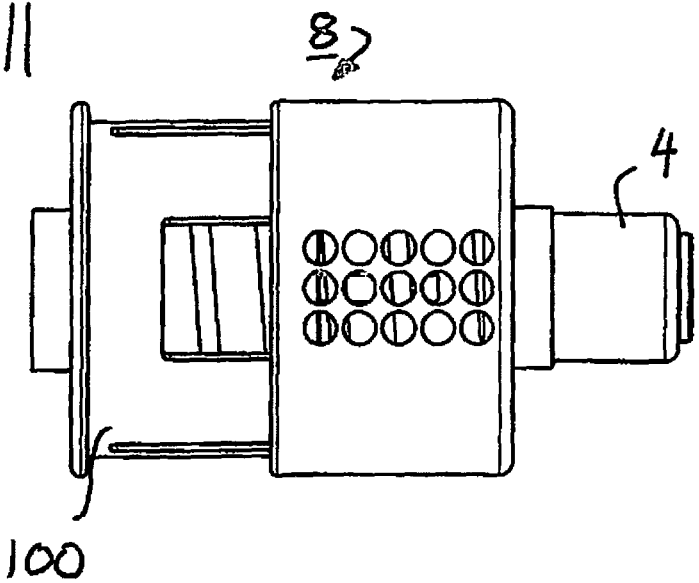
Figure 12:
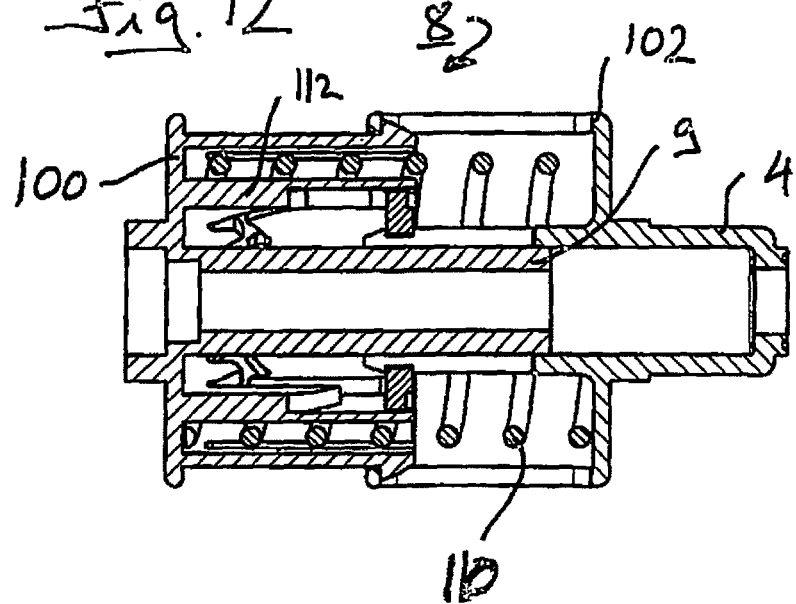
Figure 13:
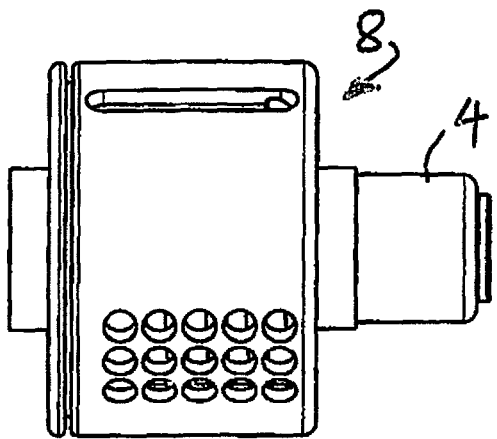
Figure 14:
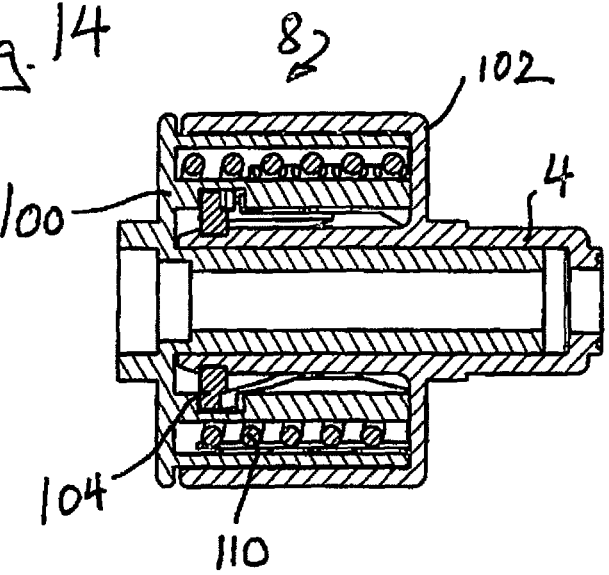

Further details, features and advantages of the invention will be explained in more detail with reference to an embodiment and to the following drawing. There are shown:

FIG. 1: a longitudinal section through an actuation mechanism in accordance with the prior art in a first position;

FIG. 2: a longitudinal section through the actuation mechanism in accordance with FIG. 1 in a second position;

FIG. 3: an installation position of the actuation mechanism;

FIG. 4: a lateral representation of a part of the actuation mechanism in accordance with the invention in accordance with a first embodiment variant;

FIG. 5: a section through the apparatus in accordance with FIG. 4;

FIG. 6: a lateral representation of the apparatus in accordance with FIG. 4 in a different position;

FIG. 7: a sectional representation through FIG. 6;

FIG. 8: a perspective exploded representation of the component in accordance with FIG. 4, FIG. 9: a detailed representation of a part in accordance with FIG. 8;

FIG. 10: a perspective detailed representation of a part in accordance with FIG. 8;

FIG. 11: a lateral representation of a part of the actuation mechanism in accordance with the invention in accordance with a different embodiment variant;

FIG. 12: a sectional representation through the apparatus in accordance with FIG. 11;

FIG. 13: a lateral representation of the apparatus in accordance with FIG. 11 in a different position;

FIG. 14: a sectional representation through FIG. 13;

FIG. 15: a perspective exploded representation of the component in accordance with FIG. 11;

FIG. 16: a detailed representation of a part in accordance with FIG. 15; and

FIG. 17: a perspective representation of a part in accordance with FIG. 15.

An actuation mechanism in accordance with the prior art is shown in FIGS. 1 to 3 such as is in particular described in detail in EP 1 154 732 A, with reference being additionally made to the description there with respect to the following statements. The actuation mechanism shown in its totality in FIGS. 1 to 3 serves the switching of an implant having two stable switching positions, in particular an artificial closure of a body passage, a body orifice or the like such as the urethra (cf. FIG. 3). The actuation mechanism 1 can likewise be implanted at a suitable point and is supported at the pubic bone 44 or at the symphysis in the case of an artificial urethra closure.

The actuation mechanism 1 has a support element 2 which is provided with an assembly plate 3 and a guide sleeve surrounded by a sheath 45. The support element 2 has a curved end section 50, whereby the actuation mechanism 1, as FIG. 3 shows, can be arranged above the pubic bone. The assembly plate 3 is provided with lateral fastening tabs which project perpendicular to the plane of the drawing and which can be fixed to the pubic bone using bone screws or the like.

A clamping plate 6 is furthermore associated with the assembly plate 3, wherein a bellows or balloon 23 composed of a physiologically compatible plastic or the like is sealingly clamped between the assembly plate 3 and the clamping plate 6 and its other edge is sealingly held at a flange 36 of an actuation element 8 which is displaceably guided in the guide sleeve 4 of the support element 2. The actuation element 8 has an inner sleeve 9 and a guide sleeve 4 between which a restoring spring 5 is arranged which acts on the actuation element 8 in the position shown in FIG. 1 in which the actuation element 8 is movable toward the support element and the mount 25 has the smallest spacing from the guide sleeve 4. The bellows 23 is drawn apart and a second bellows 24 is strongly folded between two cap nuts 38 of the mount 25 and the guide sleeve 4.

A restoring spring is provided within the bellows 24 or in its wall and counters the restoring spring 5 arranged within the first bellows 23 while being weaker than it.

In the embodiment in accordance with FIGS. 1 to 3, which is generally already known, the guide sleeve 4 is displaceably guided in the inner sleeve 9. This, as described in EP 1 154 732 A, is configured such that the actuation element 8 can adopt two stable positions. FIG. 2 shows one position, namely the maximally compressed position of the actuation element 8, with the first bellows 23 configured approximately in the manner of a balloon in FIG. 1 not being shown here for reasons of simplicity. In the representation in accordance with FIG. 2, the bellows 23 not shown in any more detail here is strongly folded, whereas the bellows 24, as shown here, is drawn far apart and the mount 25 arranged at the end of a cable line has a large spacing from the end of the guide sleeve 4. The actuation element 8 can be returned into the first stable position from the position shown in FIG. 2. The mount 25 is here again moved close to the guide sleeve 4 and the bellows 24 is folded together.

The cable 51 can be guided directly in a curved end section 50 or, as shown in FIGS. 1 and 2, can be arranged in a cable sheath if, for example, too high a friction would be present between the materials used for the cable 51 and the curved end sections 50. Since the cable sheath has to be as flexible as possible to slide with the cable 51 through the curved end section 50, the cable sheath 51 is preferably composed of spheres 52 strung together and intermediate disks 53 which each have two concave contact surfaces for the spheres 52. The intermediate disks 53 are thereby arranged with restricted pivotability on the spheres 52 and the cable line can be moved through the curved end section, as the comparison of FIGS. 1 and 2 shows.

FIG. 3 shows a preferred use of the actuation mechanism 1 for lowering a surgically raised urethra adapter, i.e. for the artificial opening and closing of a urethra 43 close to the urinary bladder. A fascia 40 serves as an artificial closure element; it is arranged beneath the urethra 43 and its two ends are fixed in the mount 25 of the actuation element 8.

In the first stable position of the implanted fascia 40 engaging beneath the urethra 43, the urethra is raised and is kinked so that a urine outflow is not possible.

When the actuation element 8 is moved into the position shown in FIG. 3 by external pressure action onto a pressure surface disposed beneath the skin 46, the spacing of the mount 25 is increased and the fascia 40 is released by this difference so that the urethra adapter is lowered and the urethra 43 is opened. This represents the second stable position of the implant (cf. FIG. 3). A repeated outer pressure action on the pressure surface initiates the restoring into the first-named position.

Two embodiments for the design of the actuation mechanism 1 in accordance with the invention are shown with reference to FIGS. 4 to 10 and 11 to 17. In the actuation mechanism in accordance with the invention, the respective actuation element 8 in accordance with FIGS. 1 to 3 has been redesigned. The remaining parts of the actuation mechanism 1, as are shown in FIGS. 1 to 3, are configured in the same manner as was described above with reference to FIGS. 1 to 3, in a manner not shown in any more detail here.

In the embodiment variant shown with reference to FIGS. 4 to 10, the guide sleeve 4 can initially be recognized which corresponds to that in accordance with FIGS. 1 and 2. The curved end section 50 adjoins it and likewise corresponds to the embodiment in accordance with FIGS. 1 to 3. The actuation element 8, as shown in FIG. 5, has an inner sleeve 9 which is displaceable in the guide sleeve 4.

A cup-shaped sleeve element 10 is arranged at the free end of the inner displaceable sleeve 9. This cup-shaped sleeve element 100 corresponds to a further cup-shaped sleeve element 102 which is connected to the guide sleeve 4 in the manner visible in accordance with FIG. 5. A guide ring 104, which cooperates with a guide link 106 which is provided in the sleeve 9, is furthermore connected to the cup-shaped sleeve element 102. In this respect, reference is made to the representation in accordance with FIG. 9 in which the corresponding guide groove 106 for the guide ring 104 can be recognized in detail. The guide ring 104 is mounted longitudinally displaceably on the guide sleeve 4 in a particularly simple manner via a snap-in element 114 which can be snapped on.

The guide ring 104 is shown in a perspective representation in FIG. 10. This guide ring has four prolongations 108 which are arranged at the inner periphery of the guide ring 104. The prolongations 108 are, as indicated here, shown as substantially triangular in cross-section, with them each having flattened corners. The corresponding prolongations 108 are arranged offset from one another and cooperate with the tooth-shaped guide groove 106 such that they slide along the guide groove by a longitudinal displacement of the components 100 and 102 and latch into corresponding latch positions there. The latch positions are selected in this respect so that the corresponding positions of the actuation mechanism 1 in FIGS. 1 and 2 can be set. In this respect, the position in accordance with FIGS. 4 and 5 of the actuation element 8 shown here corresponds to the position of the actuation element 8 in FIG. 1 and, in accordance with FIGS. 6 and 7, with the position of the actuation element 8 in FIG. 2.

So that the prolongations 108 of the guide ring 104 remain in the corresponding latch positions of the guide groove 106, a spring 110 is provided which is arranged between the sleeve elements 100 and 102 so that the sleeve element 100 can be displaced with the corresponding sleeve 9 with respect to the sleeve element 102 against the spring force 110. In this respect, after leaving the latch position, as is shown in FIGS. 4 and 5, a second latch position is reached by a corresponding compression of the components 100 and 102 by a sliding of the prolongations 108 along the guide groove 7 after reaching the position in accordance with FIGS. 6 and 7. This latch position has the effect that the sleeve 9 is pushed into the guide sleeve 4 in the manner shown in FIG. 7.

By a corresponding pressure on the component 100 against the spring force, the latch position is left again and the latch position in accordance with FIG. 5 is again reached due to a corresponding further sliding of the prolongations 108 along the guide link 106. Due to the positive guidance of the guide link 106 and of the prolongations 108 configured in accordance with its shape, the guide ring 104 rotates along the guide link 106 during the longitudinal movement of the sleeve 9 in the guide sleeve 4.

The activation part, i.e. here the mount 25 with the fascia comprising the body tube, is actuated by means of the cable 51 by the switchover of the actuation element 8 or activating part substantially consisting of the sleeves between the two latch positions.

The embodiment variant of the actuation element 8 shown with reference to FIGS. 11 to 17 corresponds in its function in turn to the actuation element 8 in accordance with the previously described embodiment variant. The same parts are provided with the same reference numerals.

The essential difference of this embodiment variant with respect to the embodiment variant previously explained with reference to FIGS. 4 to 10 comprises the guide link 106 being recessed in an intermediate sleeve 112 arranged in parallel between the sleeve 9 and the cup-shaped sleeve element 100 surrounding it. It is configured in one piece with the cut-shaped sleeve element 100 in the embodiment shown here. As is shown in FIG. 16, the guide link 106 is arranged in the intermediate sleeve 112. The guide ring 104, which has similar prolongations 108 to the guide ring shown in FIG. 10 and which is connected to the guide sleeve 4, runs in the guide link 106. As a comparison of the guide rings 104 in accordance with FIG. 17 in FIG. 10 shows, in the embodiment variant in accordance with FIG. 10, a guide ring 104 is shown whose prolongations 108 are disposed toward the interior of the guide ring, while in the embodiment in accordance with FIG. 17, it is a guide ring whose prolongations 108 are directed outwardly. The shape and arrangement of the prolongations 108 is substantially the same as in the previously described embodiment in accordance with FIG. 10.

Reference can be made to the previous description of the first embodiment in accordance with FIGS. 4 to 10 with respect to the function of the further elements of the actuation element 8 in accordance with the embodiment in accordance with FIGS. 11 to 17.

The invention claimed is:

1. An implantable actuation mechanism which can be switched between two stable positions, for an implant which can be switched between states or positions, the actuation mechanism comprising a support element which has an assembly plate for support at a bone and a spring-loaded actuation element which is movable relative to a side of the support element, which extends through the support element and which is connected to an activation part, the spring-loaded actuation element configured to initiate a change between the two positions of the implant, and the activation part provided at an opposite side of the support element, wherein the spring-loaded actuation element includes a guide ring having two or more prolongations, wherein the prolongations are guided in a guide link such that the prolongations can latch into two latch positions defining the two positions under a spring load.

2. An actuation mechanism in accordance with claim 1, wherein the guide ring is connected to a guide sleeve of the actuation element.

3. An actuation mechanism in accordance with claim 1, wherein the guide link is provided in an inner sleeve of the actuation element or in a separate intermediate sleeve connected thereto.

4. An actuation mechanism in accordance with claim 1, wherein the guide ring has an inner side and outer side and the prolongations are arranged on the inner side of the guide ring.

5. An actuation mechanism in accordance with claim 1, wherein the guide ring has an inner side and outer side and the prolongations are arranged on the outer side of the guide ring.

6. An actuation mechanism in accordance with claim 1, wherein the prolongations have a substantially triangular cross-section.

7. An actuation mechanism in accordance with claim 1, wherein the guide ring is mounted longitudinally displaceably on a guide sleeve via a snap-in element which can snap onto the guide sleeve.

8. An actuation mechanism in accordance with claim 1, wherein the guide ring has four prolongations.

9. An actuation mechanism in accordance with claim 8, wherein the guide ring has a periphery and the four prolongations are arranged equally distributed over the periphery of the guide ring.

* * * * *